United States Patent [19]

Colliver

[11] Patent Number: 5,078,685
[45] Date of Patent: Jan. 7, 1992

[54] CATHETER WITH EXTERIOR TUNNEL MEMBER

[75] Inventor: Michael D. Colliver, Pembroke Pines, Fla.

[73] Assignee: Cordis Corporation, Miami Lakes, Fla.

[21] Appl. No.: 558,583

[22] Filed: Jul. 27, 1990

[51] Int. Cl.$^5$ ............................................. A61M 29/00
[52] U.S. Cl. ........................................ 604/96; 606/194
[58] Field of Search ................. 606/191, 192, 194; 604/96–104, 264, 280, 281, 282; 128/207.14, 207.15

[56] References Cited

U.S. PATENT DOCUMENTS

| 4,183,102 | 1/1980 | Guiset | 604/101 |
| 4,289,128 | 9/1981 | Rüsch | 128/204.25 |
| 4,581,017 | 4/1986 | Sahota | 606/192 |
| 4,762,129 | 8/1988 | Bonzel | 604/96 |
| 4,877,031 | 10/1989 | Conway et al. | 606/194 |
| 4,909,252 | 3/1990 | Goldberger | 604/96 |
| 4,944,745 | 7/1990 | Sogard et al. | 604/194 |

FOREIGN PATENT DOCUMENTS 8800071  1/1988  World Int. Prop. O. .......... 606/194

Primary Examiner—C. Fred Rosenbaum
Assistant Examiner—William W. Lewis
Attorney, Agent, or Firm—Gerstman & Ellis, Ltd.

[57] ABSTRACT

A vascular catheter comprises an elongated, flexible tubular catheter body. In accordance with this invention, a relatively rigid tunnel member is carried laterally on the catheter body outside of the catheter body. The tunnel member defines an open, non-collapsible, longitudinal passageway for blood flow outside of the catheter body when the vascular catheter is inserted in a blood vessel of a patient.

17 Claims, 1 Drawing Sheet

CATHETER WITH EXTERIOR TUNNEL MEMBER

BACKGROUND OF THE INVENTION

Coronary dilatation catheters are used to forcibly expand constricted blood vessel areas, particularly the coronary arteries, by means of the pressure of an expanding balloon. Additionally, so-called "bailout perfusion catheters" are also provided to expand and push obstructions outwardly within blood vessels. For example, sometimes the blood vessel wall can collapse inwardly, this condition being called a "dissection". Also, an internal flap of the blood vessel wall may separate and move inwardly. Likewise, blood vessels can constrict due to a vasospasm. Since all of these conditions can result in a severe diminution of blood flow through the blood vessel, they can result in grave clinical injury to the patient unless the situation is remedied by a bailout perfusion catheter, which is inserted to expand the blood vessel again.

In conventional balloon catheters of the above-described type, the amount of time that the balloon can be inflated to forcibly expand the blood vessel is strictly limited, since the expanded balloon may cut off the blood supply more thoroughly than any of the above described conditions that it is attempting to alleviate. Accordingly, one must deflate the balloon, typically after 10 seconds or so of inflation time, whether or not the desired effect has been fully achieved, so that at least some blood flow can take place through the blood vessel being treated.

In Sahota U.S. Pat. No. 4,581,017 a balloon catheter is provided in which auxiliary blood flow paths flow past the balloon while the balloon is in inflated condition within a blood vessel. Thus, blood can be supplied to areas downstream of the balloon inflation through the blood vessel while the balloon remains inflated. However, the flow volume of blood that can be passed downstream is relatively small.

There remains a need for a perfusion or dilatation catheter, which can be used for dilatation in the addressing of blood vessel problems such a dissections, projecting tissue flaps, stenoses, or vasospasms, in which internal dilatation of a blood vessel can be provided while relatively high volumes of blood pass through the area of dilatation. In the Sahota patent it is apparent that only relatively small quantities of blood can pass through the dilatation area.

Also, a simplified catheter is provided by this invention which is capable of exerting a focused, somewhat asymmetrical lateral pressure on a portion of a blood vessel wall, to help reseat a tissue flap or the like during the dilatation procedure.

DESCRIPTION OF THE INVENTION

In this invention, a vascular catheter is provided which comprises an elongated, flexible, tubular catheter body. By the improvement of this invention, a relatively rigid tunnel member is carried laterally on the catheter body outside of the catheter body. The tunnel member defines an open, noncollapsible, longitudinal passageway for blood flow outside of the catheter body when the vascular catheter is inserted in a blood vessel of a patient.

Preferably, the catheter body defines an inflation lumen, and carries inflation balloon means which are positioned adjacent and substantially laterally opposite to the tunnel member. The effect of this is to provide lateral force by inflation of the balloon to press the tunnel member outwardly against the blood vessel wall in a patient, typically with a focused, lateral force because the tunnel member is made of a material that is typically more rigid than the material of the catheter body and also the material of the balloon wall. Thus, it becomes possible to counteract a blood vessel wall dissection, a projecting tissue flap, stenoses, or a vasospasm by inflation of the balloon of this invention. At the same time, blood can continue to flow freely through the tunnel member past the balloon inflation site, so that the blood vessel can continue to supply tissues downstream thereof in a manner approaching normal flow conditions.

It is to be understood that the term "blood vessel", also includes structures in and around the heart, or any other organ of the body as well as blood vessels, if it is desired to use the catheter of this invention within a body organ. Particularly, the catheter of this invention is contemplated for use in both coronary and peripheral arteries and veins.

The vascular catheter of this invention may utilize an inflation balloon which is generally of C-shaped cross section, to define a pair of longitudinal balloon wall edges. These balloon wall edges may be sealed, typically by heat sealing, to the tunnel member, which may be made of a thermoplastic material which is sealingly compatible with balloon wall material. The tunnel member and the balloon may be made of the same plastic material, if desired, such as nylon or poly(ethylene terephthalate), or any other desired plastic material, with the tunnel member typically having greater rigidity through a greater wall thickness.

Also, the tunnel member may be of generally C-shaped cross section to define a pair of longitudinal tunnel member wall edges. These edges may be sealed to the catheter body by any desired means, for example by heat sealing.

The catheter of this invention may also define a main lumen to receive a guidewire, and optionally to provide flow communication of medicaments upon removal of the guide wire, for example x-ray contrast media, anti-clotting agents, or the like.

Preferably, the tunnel member is positioned adjacent the distal end of the catheter. The tunnel member is typically no more than one tenth the overall length of the catheter, and may be substantially less than that, being generally on the order of 3 centimeters or less in length along its outermost surface.

Thus, a vascular catheter is provided in which balloon dilatation can be achieved without major occlusion of blood flow in the blood vessel where the catheter resides. Accordingly, the surgeon is not limited in the duration of dilatation which he can apply to the blood vessel area where treatment is proceeding, for greater versatility to facilitate the medical procedure. Particularly in the case of a dissection, a stenosis, an internal flap, or a vasospasm, the catheter of this invention may be particularly valuable where, as the expansion of the balloon is reduced, the dissection, stenosis, vasospasm, or internal flap may once again expand to occlude flow of blood through the blood vessel, so that, apart from this invention, deflation of the balloon does not help significantly in getting blood through the blood vessel and downstream to the tissues. By this invention, a blocked artery or vein can be opened and held open with relatively good blood flow, for temporary support of the patient until the condition can be repaired by surgery.

DESCRIPTION OF SPECIFIC EMBODIMENTS

Figure 1:
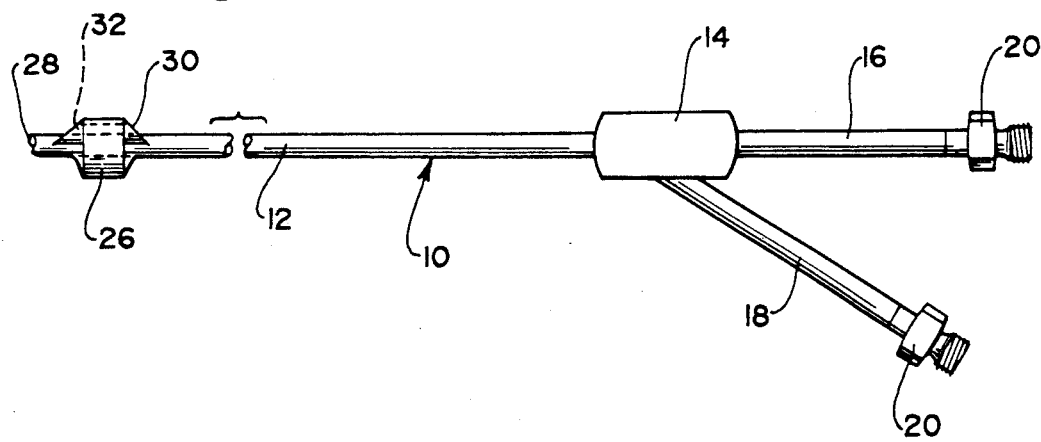
FIG. 1 is a plan view of the vascular catheter of this invention.

Referring to the drawings, vascular catheter 10 is shown, being made of a conventional catheter materials such as polyurethane or nylon, and being typically proportioned to the size of known vascular catheters such as catheters for dilatation of coronary arteries.

Catheter 10 comprises an elongated, flexible, tubular catheter body 12 defining a conventional Y connection hub 14 near its proximal end, plus a pair of branching catheter portions 16, 18 with conventional catheter proximal end ports 20. Branch portion 16 communicates with a main catheter lumen 22, which is typically proportioned to receive a guidewire, so that catheter 10 can be quickly advanced to the site of use along a preemplaced guidewire in main lumen 22.

Branched catheter portion 18 communicates with an inflation lumen 24, which communicates with catheter balloon 26. Catheter balloon 26 is shown to be in a rather idealized, as-molded configuration. In normal circumstances the shape of flexible balloon 26 will of course not hold the sharp, straight line configuration as indicated in the drawings because of its inherent flexibility.

Figure 2:
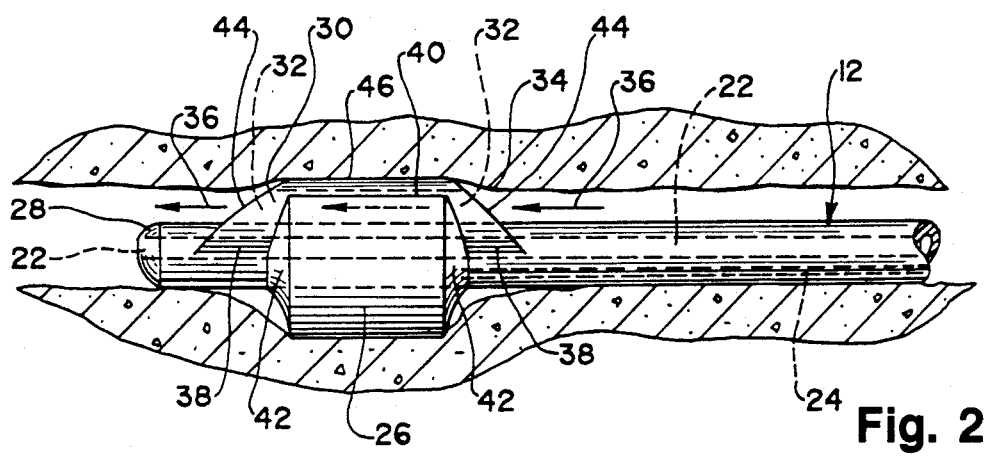
FIG. 2 is an enlarged, plan view of the distal end of the vascular catheter of FIG. 1, showing the catheter emplaced in an artery of a patient.

In accordance with this invention, catheter body 12 carries, adjacent its distal end 28, a relatively rigid tunnel member 30, defining a tunnel aperture 32 which extends longitudinally from end to end thereof. Tunnel member 30 may be made of a plastic material which is sealingly compatible with both the plastic material of catheter body 12 and the plastic material of balloon 26. The wall thickness of tunnel member 30 is sufficient to cause the tunnel member to be relatively rigid, when compared with the flexible catheter body 12 and balloon 26, with the amount of rigidity being sufficient to greatly resist collapse of the tunnel member when it is pressed outwardly against a wall 34 of a blood vessel, as particularly shown in FIG. 2. Thus, as tunnel member 30 is pressed outwardly by inflated balloon 26, it can counteract a dissection, projecting tissue flap, stenoses, or vasospasm in the blood vessel wall 34, while at the same time blood can flow in the direction indicated by arrows 36 through the aperture 32 of tunnel member 30.

Figure 3:
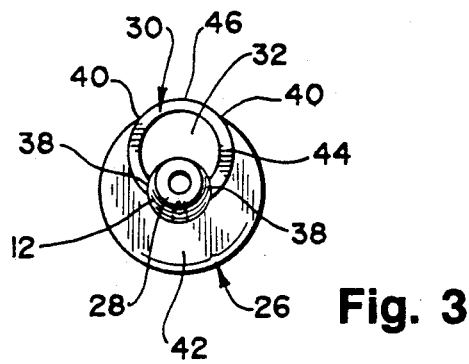
FIG. 3 is an elevational view of the distal end of the catheter of FIG. 1.

As shown in FIG. 3, tunnel member 30 may be of generally C-shaped cross section to define a pair of longitudinally extending tunnel member wall edges 38. These edges may be sealed, for example by heat sealing, to catheter body 12.

Likewise, balloon 26 may be generally of a C-shaped cross section as also shown in FIG. 3, to define a pair of longitudinal balloon wall edges 40. These edges may be heat sealed to tunnel member 30. Additionally, end portions 42 of balloon 26 may be correspondingly heat sealed to tunnel member 30 and catheter body 12, to provide a sealed, inflatable balloon which may be roughly of a cylindrical section in shape when inflated, but missing a longitudinal portion of a cylinder, the volume of which is occupied by tunnel member 30.

It can be seen that balloon member 26 is positioned adjacent and substantially laterally opposite to tunnel member 30, to provide lateral force to the tunnel member by inflation of the balloon, to press the tunnel member outwardly against blood vessel wall 34 as the balloon presses in other lateral directions.

Also, it can be seen that the open end surfaces 44 of tunnel member 30 can be sloped to provide an angled face, so that the length of tunnel member wall edges 38 may be greater than the length of the outermost area 46 of tunnel member 30. By this, good adhesion of tunnel member 30 to the catheter can be achieved, while at the same time the general area of the outermost section 46 of the tunnel member can be reduced, typically to an area having a length the approximates the length of balloon 26, so that the outermost area 46 of the tunnel member can be forcefully pressed with desired higher pressure per unit area against blood vessel wall 34 by expansion of balloon 26.

Typically, tunnel member 30 may be about two centimeters in length along area 46, with the catheter 10 being otherwise dimensioned in a manner typical for cardiac dilatation catheters.

Thus, the catheter of this invention provides a reliable means for performing dilatation, to attempt to remedy any of several serious medical conditions in a blood vessel, while permitting a good flow of blood to pass through the blood vessel, as evidenced by flow arrows 36.

The above has been offered for illustrative purposes only, and is not intended to limit the scope of the invention of this application, which is as defined in the claims below.

That which is claimed is:

1. In a catheter which comprises an elongated, flexible, tubular catheter body, the improvement comprising, in combination:

a relatively rigid tunnel member carried laterally on the catheter body outside of said catheter body, said tunnel member defining an open, non-collapsible, longitudinal passageway for blood flow outside of said catheter body when said catheter is inserted in a blood vessel of a patient, said catheter body defining an inflation lumen and carrying inflation balloon means positioned adjacent and substantially laterally opposite to said tunnel member, to provide lateral force by inflation of said balloon to press said tunnel member outwardly against a blood vessel wall in a patient, to counteract a blood vessel wall dissection, projecting tissue flap, stenosis, or vasospasm.

2. The catheter of claim 1 in which said inflation balloon is generally of C-shaped cross section to define a pair of longitudinal balloon wall edges, said edges being sealed to said tunnel member.

3. The catheter of claim 2 in which said tunnel member is generally of C-shaped cross section to define a pair of longitudinal tunnel member wall edges, said edges being sealed to said catheter body.

4. The catheter of claim 1 in which said tunnel member is generally of C-shaped cross section to define a pair of longitudinal tunnel member wall edges, said edges being sealed to said catheter body.

5. The catheter of claim 1 which defines a main lumen to receive a guidewire and to otherwise provide flow communication of medicaments.

6. The catheter of claim 1 in which said tunnel member is positioned adjacent the distal end thereof, the length of said tunnel member being no more than one tenth the overall length of the catheter.

7. The catheter of claim 1 in which said tunnel member is generally of C-shaped cross section to define a pair of longitudinal tunnel member wall edges, said edges being sealed to said catheter body, said tunnel member wall edges being sloped inwardly so that the length of said longitudinal tunnel member wall edges is greater than the length of portions of said tunnel member which are radially outward therefrom relative to the axis of said catheter.

8. The catheter of claim 1 in which said tunnel member has solid walls.

9. In a catheter which comprises an elongated, flexible, tubular catheter body, the improvement comprising, in combination:

a relatively rigid tunnel member carried laterally on the catheter body outside of said catheter body, said tunnel member defining an open, noncollapsible, longitudinal passageway for blood flow outside of said catheter body when said catheter is inserted in a blood vessel of a patient, said catheter body defining an inflation lumen and said catheter body carrying inflation balloon means positioned adjacent and substantially laterally opposite said tunnel member, to provide lateral force by inflation of said balloon to press said tunnel member outwardly against the blood vessel wall in a patient, to expand said blood vessel wall, in which said tunnel member is generally of C-shaped cross section to define a pair of longitudinal tunnel member wall edges, said edges being sealed to said catheter body.

10. The catheter of claim 9 in which said tunnel member is positioned adjacent the distal end thereof, the length of said tunnel member being no more than one tenth the overall length of the catheter.

11. The catheter of claim 10 which defines a main lumen to receive a guidewire and to otherwise provide flow communication of medicaments.

12. The catheter of claim 11 in which said inflation balloon is generally of C-shaped cross section to define a pair of longitudinal balloon wall edges, said edges being sealed to said tunnel member.

13. The catheter of claim 12 in Which said tunnel member wall edges are sloped inwardly so that the length of said longitudinal tunnel member wall edges is greater than the length of portions of said tunnel member which are radially outward therefrom relative to the axis of said catheter.

14. In a vascular catheter which comprises an elongated, flexible, tubular catheter body, the improvement comprising, in combination:

a relatively rigid tunnel member carried laterally on the catheter body outside of said catheter body, said tunnel member defining an open, non-collapsible, longitudinal passageway for blood flow outside of said catheter body when said vascular catheter is inserted in a blood vessel of a patient, said tunnel member being positioned adjacent the distal end of said catheter body, the length of said tunnel member being no more than one tenth the overall length of the catheter, said catheter body defining an inflation lumen and said catheter body carrying inflation balloon means positioned adjacent and substantial laterally opposite to said tunnel member, to provide lateral force by inflation of said balloon to press said tunnel member outwardly against the blood vessel wall in a patient, to counteract a blood vessel wall dissection, projecting tissue flap, stenosis, or vasospasm.

15. The vascular catheter of claim 14 in which said inflation balloon is generally of C-shaped cross section to define a pair of longitudinal balloon wall edges, said edges being sealed to said tunnel member.

16. The vascular catheter of claim 15 in which said tunnel member is generally of C-shaped cross section to define a pair of longitudinal tunnel member wall edges, said edges being sealed to said catheter body.

17. The catheter of claim 16 in which said tunnel member wall edges are sloped inwardly so that the length of said longitudinal tunnel member wall edges is greater than the length of portions of said tunnel member which are radially outward therefrom relative to the axis of said catheter.

* * * * *